(12) United States Patent
Ogden et al.

(10) Patent No.: US 6,390,995 B1
(45) Date of Patent: May 21, 2002

(54) METHOD FOR USING ACOUSTIC SHOCK WAVES IN THE TREATMENT OF MEDICAL CONDITIONS

(75) Inventors: John A. Ogden, Atlanta; John F. Warlick, Woodstock, both of GA (US)

(73) Assignee: Healthtronics Surgical Services, Inc., Marietta, GA (US)

( * ) Notice: Subject to any disclaimer, the term of this patent is extended or adjusted under 35 U.S.C. 154(b) by 0 days.

(21) Appl. No.: 09/342,151

(22) Filed: Jun. 25, 1999

Related U.S. Application Data

(60) Continuation-in-part of application No. 09/120,267, filed on Jul. 21, 1998, now abandoned, which is a continuation-in-part of application No. 08/799,585, filed on Feb. 12, 1997, now abandoned, which is a continuation-in-part of application No. 09/427,686, filed on Dec. 23, 1998, which is a division of application No. 08/799,585, filed on Feb. 12, 1997.

(51) Int. Cl.$^7$ .............................................. A61B 17/22
(52) U.S. Cl. .......................................... 601/2; 600/427
(58) Field of Search ................................ 600/427, 439; 601/2–4

(56) References Cited

U.S. PATENT DOCUMENTS

| | | |
|---|---|---|
| 2,559,227 A | 7/1951 | Rieber |
| 3,499,437 A | 3/1970 | Balamuth |
| 3,776,223 A * | 12/1973 | Yeager et al. ............... 601/157 |
| 3,942,531 A | 3/1976 | Hoff et al. |
| 4,530,360 A | 7/1985 | Duarte |
| 4,669,472 A | 6/1987 | Eisenmenger |
| 4,802,525 A | 2/1989 | Heine et al. |
| 4,805,600 A | 2/1989 | Wess et al. |
| 4,809,682 A | 3/1989 | Forssmann et al. |

(List continued on next page.)

FOREIGN PATENT DOCUMENTS

| | | |
|---|---|---|
| DE | 4036981 | 5/1992 |
| DE | 19718513 | 5/1998 |
| DE | 19718512 | 6/1998 |
| EP | 0324163 | 7/1989 |
| EP | 0324711 A2 | 7/1989 |
| EP | 0450423 | 1/1997 |
| WO | WO 96/09621 | 3/1996 |

OTHER PUBLICATIONS

Maffulli, Nicola et al., "Overuse Tendon Conditions: Time to Change a Confusing Terminology," *Arthroscopy: The Journal of Arthroscopic & Related Surgery*, Nov./Dec. 1998, vol. 14, No. 8, pp. 840–843.

Guerkov, H.H. et al., "Pulsed Electromagnetic Fields Increase Growth Factor Release by Nonunion Cells," *Clinical Orthopaedics and Related Research*, Mar. 2001, No. 384, pp. 265–270.

Dahman, G.P. et al., "Extrakororale Stosswellentherapie (ESWT) zur Behandlung von Knockennahen Weichteilschmerzen: Indikation. Technik und Vorläufige Ergenbnisse," in Attempto Medizin und Technik. Jg. 1993. S. 143 bis 148 Attempto Verlag Tübingen GmBH (including English translation thereof).

(List continued on next page.)

*Primary Examiner*—Ruth S. Smith
(74) *Attorney, Agent, or Firm*—John S. Pratt, Esq.; Camilla C. Williams, Esq.; Kilpatrick Stockton LLP

(57) ABSTRACT

This invention relates to methods for medical treatment of a variety of pathological conditions associated with bone environments and musculoskeletal environments, including the treatment of ischemic conditions such as bursitis. The method involves applying a sufficient number of acoustic shock waves to the site of a pathological condition including micro-disruptions, non-osseous tissue stimulation, increased vascularization, and circulation and induction of growth factors to induce or accelerate the body's natural healing processes and responses.

6 Claims, 2 Drawing Sheets

U.S. PATENT DOCUMENTS

| | | | |
|---|---|---|---|
| 4,887,600 A | 12/1989 | Watson et al. | 606/128 |
| 4,896,673 A | 1/1990 | Rose et al. | |
| 4,905,671 A | 3/1990 | Senge et al. | |
| 4,905,672 A | 3/1990 | Schwarze et al. | |
| 4,924,858 A | 5/1990 | Katona | |
| 4,938,232 A | 7/1990 | Wess et al. | |
| 4,940,050 A | 7/1990 | Forssmann et al. | |
| 4,979,501 A | 12/1990 | Valchanov et al. | |
| 4,998,528 A | 3/1991 | Erhardt | |
| 5,070,861 A | 12/1991 | Einars et al. | |
| 5,071,422 A | 12/1991 | Watson et al. | 606/128 |
| 5,072,721 A | 12/1991 | Weiler et al. | |
| 5,078,124 A | 1/1992 | Viebach et al. | |
| 5,119,801 A | 6/1992 | Eizenhoefer et al. | |
| 5,137,014 A | 8/1992 | Boehm | |
| 5,152,289 A | 10/1992 | Viebach et al. | |
| 5,172,692 A | 12/1992 | Kulow et al. | |
| 5,174,280 A | 12/1992 | Gruenwald et al. | |
| 5,176,675 A | 1/1993 | Watson et al. | 606/15 |
| 5,178,135 A | 1/1993 | Uchiyama et al. | |
| 5,178,136 A | 1/1993 | Wess et al. | |
| 5,181,512 A | 1/1993 | Viebach et al. | |
| 5,191,560 A | 3/1993 | Lobentanzer et al. | 362/175 |
| 5,191,880 A | 3/1993 | McLeod et al. | |
| 5,195,508 A | 3/1993 | Müller et al. | |
| 5,199,420 A | 4/1993 | Artmeier | |
| 5,209,222 A | 5/1993 | Viebach et al. | |
| 5,211,160 A | 5/1993 | Talish et al. | |
| 5,224,468 A | 7/1993 | Grünewald et al. | |
| 5,240,000 A | 8/1993 | Herrmann et al. | |
| 5,240,005 A | 8/1993 | Viebach | |
| 5,259,384 A | 11/1993 | Kaufman et al. | |
| 5,269,306 A | 12/1993 | Warnking et al. | |
| 5,284,143 A | 2/1994 | Rattner | |
| 5,287,856 A | 2/1994 | Treiber | |
| 5,309,898 A | 5/1994 | Kaufman et al. | 601/2 |
| 5,316,000 A | 5/1994 | Chapelon et al. | |
| 5,327,890 A | 7/1994 | Matura et al. | |
| 5,347,997 A | 9/1994 | Weiler et al. | 601/3 |
| 5,374,236 A | 12/1994 | Hassler | 601/2 |
| 5,393,296 A | 2/1995 | Rattner | 601/2 |
| 5,409,446 A | 4/1995 | Rattner | 601/4 |
| 5,419,327 A | 5/1995 | Rohwedder et al. | |
| 5,431,641 A | 7/1995 | Grözinger et al. | 604/283 |
| 5,458,130 A | 10/1995 | Kaufman et al. | |
| 5,458,652 A | 10/1995 | Uebelacker | 601/4 |
| 5,505,729 A | 4/1996 | Rau | 606/40 |
| 5,524,620 A | 6/1996 | Rosenchein | |
| 5,545,124 A | 8/1996 | Krause et al. | 601/2 |
| 5,595,178 A | 1/1997 | Voss et al. | |
| 5,688,263 A | 11/1997 | Hauptmann et al. | 606/13 |
| 5,692,509 A | 12/1997 | Voss et al. | |
| 5,720,762 A | 2/1998 | Bass | 606/192 |
| 5,727,556 A | 3/1998 | Weth et al. | |
| 5,810,748 A | 9/1998 | Ueberle | 601/4 |
| 5,921,930 A | 7/1999 | Überle | 600/439 |
| 5,941,838 A | 8/1999 | Eizenhöfer | 601/2 |
| 6,066,123 A * | 5/2000 | Li et al. | 604/507 |
| 6,186,963 B1 | 2/2001 | Schwarze et al. | 601/2 |
| 6,190,336 B1 | 2/2001 | Duarte et al. | 601/2 |

OTHER PUBLICATIONS

Almekinders, Louis C., "Tendinitis and Other Chronic Tendinopathies," *Journal of the American Academy of Orthopaedic Surgeons*, May/Jun. 1998, vol. 6, No. 3, pp. 157–164.

Nakano, Kenneth K., "Peripheral nerve entrapments, repitive strain disorder, occupation–related syndromes, bursitis, and tendonitis," *Current Opinion in Rheumatology*, 1991, vol. 3, No. 2, pp. 226–239.

Stell, Ian M., "Management of acute bursitis: outcome study of a structured approach," *Journal of the Royal Society of Medicine*, Oct. 1999, vol. 92, No. 10, pp. 516–521.

Lin, Jian–Hao et al., "Temporal expression of nitric oxide synthase isoforms in healing Achilles tendon," *Journal of Orthopaedic Research*, No. 19 (2001), pp. 136–142.

Dahmen, G.P. et al., "Extracorporeal Shock Wave Therapy in the Area of Bones, Specifically Soft Tissue Area of the Shoulder," *Extracta Orthopaedica*, vol. 15, No. 11, pp. 25–27.

Final Programme and Abstracts from European Society for Musuloskeletal Shockwave Therapy, London, England, May 27–29, 1999 pp. 1–65.

* cited by examiner

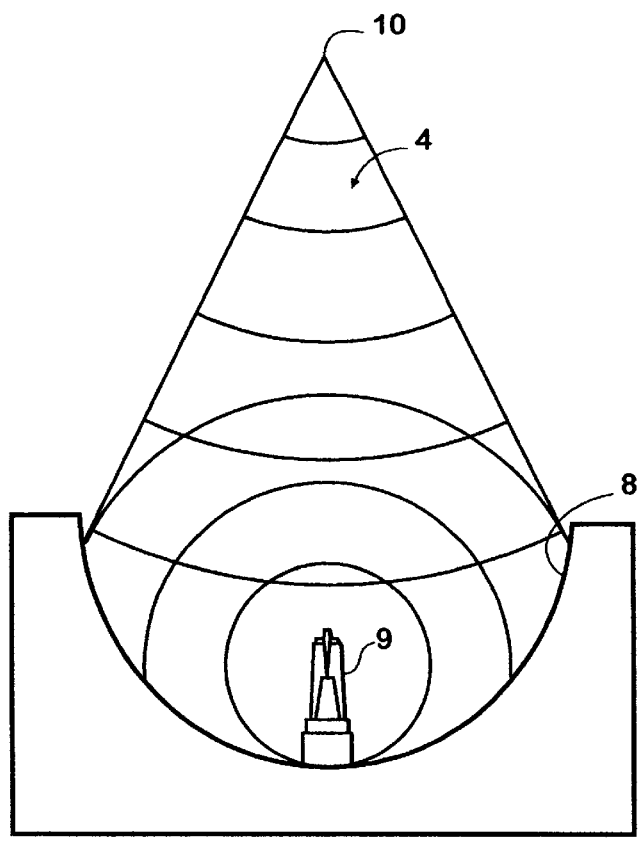
FIG.1
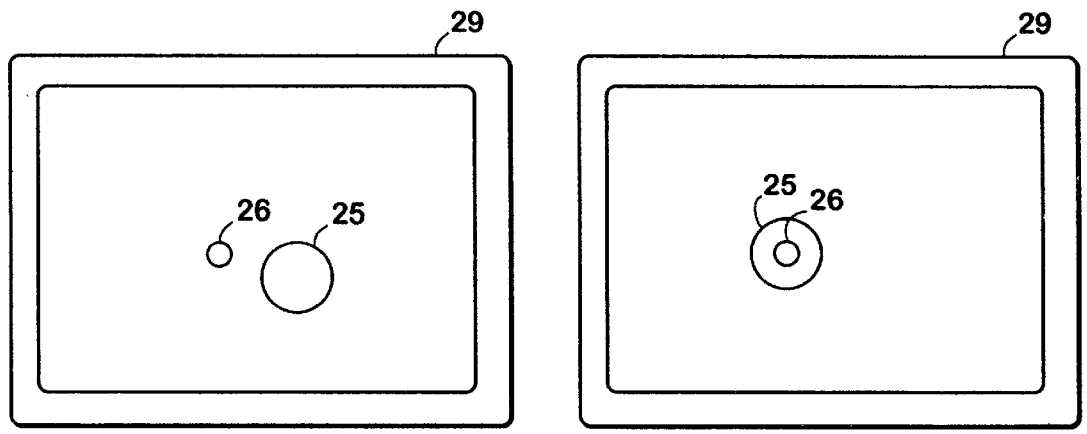
FIG.4 FIG.5

METHOD FOR USING ACOUSTIC SHOCK WAVES IN THE TREATMENT OF MEDICAL CONDITIONS

CROSS-REFERENCE TO RELATED APPLICATIONS

This application is a continuation-in-part of U.S. application Ser. No. 09/120,267, filed Jul. 21, 1998, now abandoned, which is a continuation-in-part of U.S. application Ser. No. 08/799,585, filed Feb. 12, 1997, now abandoned; and this application is also a continuation-in-part of U.S. application Ser. No. 09/427,686, filed Dec. 23, 1998, now pending, which is a divisional of U.S. application Ser. No. 08/799,585, filed Feb. 12, 1997, the entire contents of the above applications being hereby incorporated by reference.

BACKGROUND OF THE INVENTION

1. Field of the Invention

This invention relates to methods for medical treatment of pathological conditions. More particularly, the invention relates to methods for using acoustic shock waves to treat a variety of pathological conditions associated with bone environments and musculoskeletal environments (including cartilage, ligaments, fascia, tendons, joint capsules, bone marrow and muscle).

2. Description of Related Art

The use of energy wave forms for medical treatment of various bone pathologies is known in the art. For example, U.S. Pat. No. 4,530,360, issued on Jul. 23, 1985 to Duarte, teaches the use of ultrasound transducers, in direct contact with the skin of the patient, for transmitting ultrasound pulses to the site of the bone defect. Duarte teaches a nominal ultrasound frequency of 1.3 to 2.0 MHz, a pulse width range of 10 to 2000 microseconds, and a pulse rate varying between 100 and 1000 Hz Duarte maintains the ultrasound power level below 100 milliwatts per square centimeter, with treatments lasting no more than 20 minutes per day. Other devices utilize piezoelectric materials fastened adjacent to the pathological site on the patient's limb to produce ultrasonic energy in the vicinity of the bone pathology for administering therapy. Examples of such prior art references include U.S. Pat. Nos. 5,211,160, 5,259,384, and 5,309,898.

Clinicians have also utilized shock waves to treat various pathologies. Early approaches of using shock waves for medical treatment required immersing the patient in water and directing a shock wave, generated by an underwater spark discharge, at a solid site to be treated, such as a bone or kidney stone. When the shock wave hits the solid site, a liberation of energy from the change of acoustic impedance from water to the solid site produces pressure in the immediate vicinity of the site. For example, U.S. Pat. No. 4,905,671 to Senge et al., issued on Mar. 6, 1990, teaches a method applying acoustic shock waves to induce bone formation. Senge et al. teaches that the acoustical sound waves utilized by Duarte (and similar references) for treatment of bone have a generally damped sinusoidal wave form centered on ambient pressure. More specifically, Senge et al. teaches that the pressure of an acoustical sound wave utilized by Duarte rises regularly to a maximum value above ambient, falls regularly through ambient and on to a minimum value below ambient in a continued oscillation above and below ambient until complete damping occurs. Portions of the wave above ambient represent acoustic compression, while portions below ambient represent acoustic tension.

Senge et al. differentiates an idealized shock wave from the acoustic sound wave of Duarte as having a single pressure spike having a very steep onset, a more gradual relaxation, and virtually no oscillation to produce acoustic tension. Furthermore, Senge et al. teaches that the absence of extensive tension wave components allows the shock wave form to pass through soft tissue to cause controlled trauma within a designated bone sight. Senge et al. also teaches the minimization of the amplitude and extent of tension components in the wave forms for the treatment of bone.

Senge et al. utilizes the extremely short rise time of the shock wave to create high compression zones within bone tissue to cause reactions of the microcompartments of the bone. Senge et al. purports that such reactions cause the formation of hematomas within bone, which in turn, induce the formation of new bone. Senge et al. utilizes a shock wave source consisting of a spark gap between electrodes within a container of water. An electrical condenser connected to the electrodes releases its energy over a very short period of time, and an arc arises between the electrodes of the spark gap device which vaporizes water surrounding the spark's path, establishing a plasma-like state. The result is an explosion-like vaporization of the water which produces an electro-hydraulic shock wave that spreads out in a circular fashion. A metallic, ellipsoid-shaped structure surrounds a rear portion of the spark gap, opposite the patient, to produce a known focal point for positioning within the patient's pathological bone site. This device also requires that the patient be submerged in the water.

Additionally, U.S. Pat. No. 4,979,501 to Valchanov et al., issued on Dec. 25, 1990, teaches a method and apparatus for treating both pathologies with shock or "impact" waves for correction of delayed bone consolidation and bone deformations. The method disclosed in Valchanov et al. comprises the steps of anesthetizing the patient, fixing the limb affected with the pathological bone condition, centering the pathological site of the bone on the shock wave focal point, treating the affected bone site once or consecutively, with 300 to 6000 impacts having a frequency of 0.4–4.0 per second with a pulse duration of 0.5 to 4.0 microseconds for a period of 10–120 minutes, and subsequently immobilizing the limb for a period from 15 to 90 days. The impact wave generating device disclosed by Valchanov et al. generally consists of a vessel which contains a transmitting medium or acoustic liquid such as water contained therein. At a bottom portion of the vessel are opposed electrodes which are adapted to produce a shock across the gap. Therefore, the patient is not submerged for treatment.

Other references teach the treatment of bone pathologies utilizing shock wave therapy in combination with imaging means for localizing the pathology during treatment. Those references include U.S. Pat. Nos. 5,284,144, 5,327,890, 5,393,296, 5,409,446, and 5,419,327. Finally, if the number and magnitude of the shock wave pulses are sufficient, the shock wave treatment may disintegrate a kidney stone. For example, U.S. Pat. No. 4,896,673 to Rose et al., teaches a method and apparatus utilizing focused shock wave treatment of kidney stones in combination with localization using ultrasound or x-ray imaging.

Still other devices utilize transducers for producing ultrasonic waves for therapy of soft tissue. For example, U.S. Pat. No. 5,316,000 to Chapelon et al. teaches an array of composite piezoelectric transducers for making an acoustic or ultrasonic therapy device for use in the treatment of varicose veins. Similarly, U.S. Pat. No. 5,458,130 to Kaufman et al. also purports to therapeutically treat soft tissue such as cartilage, ligament, and tendons using a piezoelectric transducer excited by a composite sine-wave signal with a magnitude as may be prescribed by a physician. Thus, past methods for treating soft tissue surrounding bone utilized a transducer for the generation of ultrasonic waves for wave propagation into the pathological site within the soft tissue area. Furthermore, as described by Senge et al., clinicians traditionally implemented shock wave therapy for the treatment of bone.

Therefore, it is an object of the present invention to provide a rapid, time restricted and effective shock wave therapy treatment for pathological conditions associated with bone and musculoskeletal environments. Other objects and features of the present invention will be more readily understood from the following detailed description.

SUMMARY OF THE INVENTION

This invention relates to methods for medical treatment of pathological conditions. More particularly, the invention relates to methods for using acoustic shock waves to treat a variety of pathological conditions associated with bones and musculoskeletal environments (including cartilage, ligaments, fascia, tendons, joint capsules, bone marrow and muscle) such as neoplasm, neoplastic disease, incontinence, impotence, heart disease, liver disease, kidney disease, and ischemic conditions, including cardiac ischemia, hepatic ischemia, renal ischemia, and bursitis. The invention also relates to methods for using acoustic shock waves to augment chemotherapy and radiation therapy. This invention also relates to methods for using acoustic shock waves to treat peripheral nerve injuries and syndromes such as Morton's neuroma, post traumatic neuroma, cubital tunnel syndrome, and tarsal tunnel syndrome. The invention also relates to methods for using acoustic shock waves to treat damaged, scarred or unhealthy tissue, including such tissue in muscles or mono-cellular structures in the treatments of heart disease, liver disease and kidney disease. This invention relates to using acoustic shock waves to induce arthrodesis of the joint, such as in the case of a delayed or nonunion of a surgical fusion of a joint, and to treat insufficient or immature bone in the lengthening gap of a bone being elongated. This invention also relates to using acoustic shock waves to treat abnormal or painful scarring along pin tracts, consequent to the use of external fixation.

The present invention comprises a method of applying acoustical shock waves to the site of a pathological condition associated with a bone or musculoskeletal environment to induce, reactivate or accelerate the body's natural healing processes, especially through natural cellular and molecular (macromolecular) biologic responses, including the stimulation of tissue specific group factors (cytokines, morphogenetic proteins), and to improve local microcirculation through activated neoangiogenesis. The method according to the present invention may also include the steps of locating the site of a pathological condition, generating acoustic shock waves, focusing the acoustic shock waves on the pathological site, and applying the focused acoustical shock waves on the site to induce localized trauma and cellular apotosis therein, including micro-fractures, as well as to induce osteoblastic responses such as cellular recruitment, stimulate formation of molecular bone, cartilage, tendons, fascia and soft tissue morphogens and growth factors, and to induce vascular neoangiogenisis. The method similarly induces in musculoskeletal environment tissues neoangiogenesis and the formation, recruitment or stimulation of tissue specific morphogenetic macromolecules and growth factors.

Micro-disruptions resulting from the shock wave therapy induce cellular changes, and extracellular matrix and macromolecular changes in a controlled fashion for the purpose of stimulating increased neoangiogenesis leading to adequate vascularization in ischemic tissues. The increased circulation and vascularization then induce the body's natural cellular (tissue specific) healing processes. The accompanying cellular changes lead to or are associated with elaboration and production of bone and tissue morphogenetic proteins, known as growth factors.

For the purposes of this specification, the bone and musculoskeletal environments may include the cartilage, tendons, ligaments, joint capsules, fascia, synovium, muscles, and neural elements, for example proprioceptors and nociocepters, which functionally support skeletal structures.

The inventive method may be used to treat pathological conditions such as neoplasm, incontinence, impotence, heart disease, liver disease and kidney disease. The neoplasm treated may include neuroma formation. The inventive method may also be used as therapy augmentation for either radiation therapy, chemotherapy, or limb salvage. The heart disease, liver disease and kidney disease treated by the inventive method may include cardiac ischemia, hepatic ischemia and renal ischemia. The inventive method may also be used to treat other ischemic conditions. The inventive method may be used to treat peripheral nerve injuries and syndromes and to induce arthrodesis of the joint.

The method according to the present invention may also be used to treat a pathological condition associated with soft tissue adjacent to a musculo-skeletal environment characterized by the presence of scarred or unhealthy tissue. The scarred or unhealthy tissue may be located in muscles or mono-cellular structures.

The method according to the present invention may utilize physical palpation, X-ray image intensification, CT direction, or ultrasonography to precisely locate the pathological site. Once the site is located, the inventive method may utilize an ellipsoid reflector or focusing lens to specifically direct the acoustic shock waves to the impact (treatment) site.

BRIEF DESCRIPTION OF THE DRAWINGS

FIG. 1 is a schematic representation of a shock wave generation device with a focusing mechanism used in accordance with the inventive method.

FIGS. 4 and 5 illustrate schematic representations of monitors that display images of alignment targets for the therapy head in unaligned and aligned positions, respectively.

DETAILED DESCRIPTION OF THE SPECIFIC EMBODIMENTS

Implementation of the method of the present invention requires the use of a locating device or palpation to locate the pathological site. Locating devices may include, but are not limited to X-ray or ultrasound machines. For example, the method and apparatus described in U.S. Pat. No. 4,896, 673 to Rose et al., issued Jan. 30, 1990, the disclosure of which is incorporated herein in its entirety, may be used according to this invention locate the pathological site.

The method also typically requires a shock wave source, such as a spark gap generator. Suitable spark gap generators are described in U.S. Pat. Nos. 4,905,671 to Senge et al.; 4,979,501 to Valchanov et al.; 5,284,143 to Rattner; 5,327,890 to Matura et al.; 5,393,296 to Rattner; 5,409,446 to Rattner; and 5,419,327 to Rohwedder et al., the disclosures of which are hereby incorporated by reference. The method according to the present invention may also utilize the electromagnetic shock wave source and parabolic wave focusing means of the type described in U.S. Pat. No. 5,327,890 to Matura et al., the disclosure of which is hereby incorporated by reference. The focusing means may also comprise parabolic reflectors utilized in kidney lithotripters.

The method typically requires use of apparatus for focusing the acoustic shock waves with an appropriate device, such as an ellipsoid or parabolic focusing lens. The reflector is generally located in a therapy head, which directs the waves to a focal point. FIG. 1 is a schematic representation of such a shock wave generator and focusing means. Shock waves 4 radiate from electrode 9 and through water (not shown). Waves 4 reflect from ellipsoid surface 8 and toward focal point 10.

Figure 2:
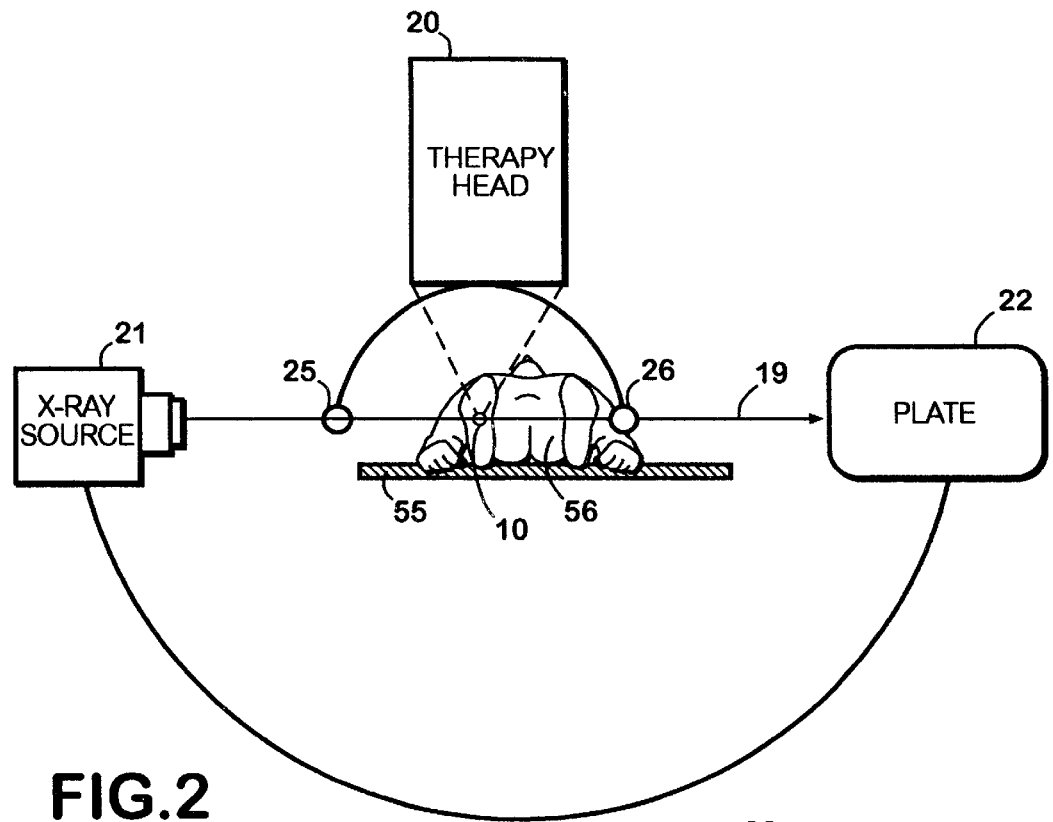
FIG. 2 is a schematic representation of a therapy head and locating mechanism used in accordance with the inventive method.
Figure 3:
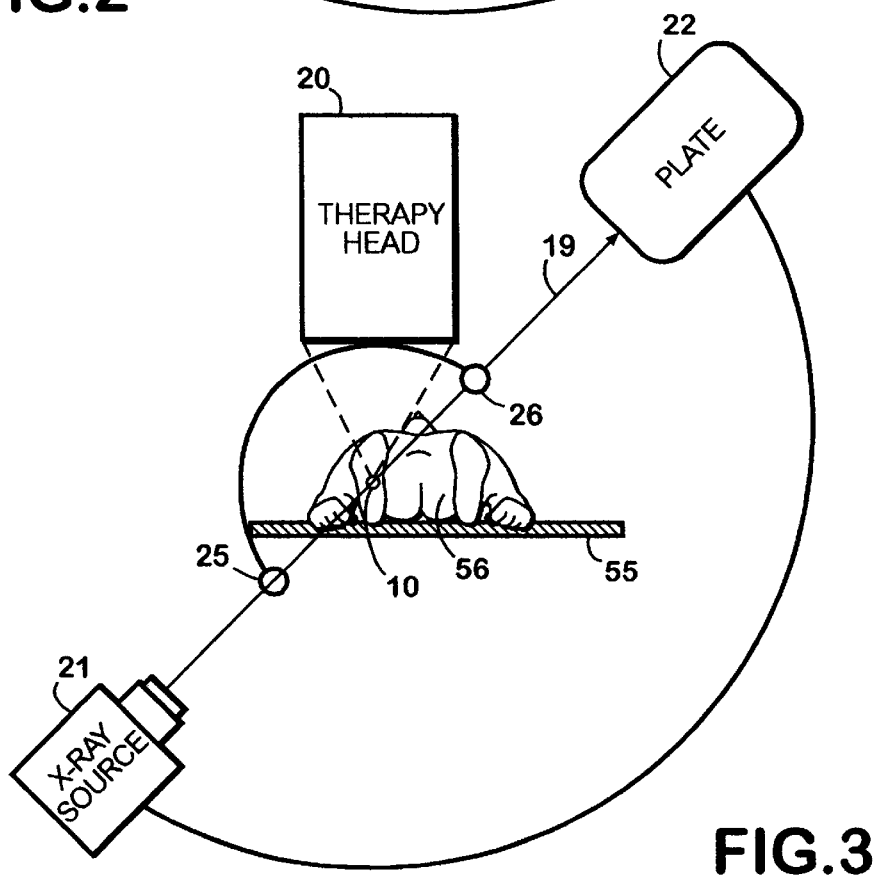
FIG. 3 is a schematic representation of the therapy head and locating mechanism illustrated in FIG. 2 with the locating mechanism orientated at a 45 degree angle with respect to a horizontal plane.

In a preferred embodiment, the therapy head also includes a targeting device which functions in conjunction with an X-ray machine locating device, as is illustrated in FIGS. 2 and 3 or other appropriate locating device. FIGS. 2 and 3 schematically illustrate a patient 56 positioned on a surface 55 during a treatment session. Two movable targets 25 and 26 are connected mechanically to the therapy head 20 so that the pair of targets 25 and 26 may rotate around at least two different axes with an imaginary connecting line 19. An X-ray source 21 and plate 22 define a connecting line 19 which passes through the targets 25 and 26. Connecting line 19 always extends between the two targets and throughout the focal point 10 of the shock waves. Before beginning treatment in accordance with the present invention, the clinician aligns the tissue area to be treated with the approximate center of an X-ray image being projected by the source 21. An appropriate monitor 29 illustrates the projection of the X-ray image as illustrated in FIGS. 4 and 5. As illustrated in FIG. 4, when targets 25 and 26 do not coincide with one another, then focal point 10 is not aligned with the treatment site. After proper alignment, as shown in FIG. 5, the targets 25 and 26 coincide with the treatment site, and the clinician may begin treatment. As illustrated in FIG. 3, the imaging mechanism may also be positioned at various angles with respect to the patient depending on the location of the treatment site within the patient. Alternatively, an ultrasound locating unit positions the shock wave focal point between the patient's pathological site and the acoustically reflective object.

Particular applications of the method are illustrated in the following examples.

The inventive method may include a wide range in the various parameters used to treat all of the pathologies mentioned in this specification. Specifically, for each of the pathologies mentioned in this specification, the inventive method may include applying a range of approximately 14–28 kilovolts of energy per pulse; the pulse frequency may be approximately 0.5–5 Hz (pulses/sec) and the pulse duration may be approximately 280 ns. The number of pulses per treatment should be approximately 500–10,000, and the total time per treatment should be approximately 5 minutes to 2 hours. Additionally, the number of treatments necessary for a positive response may vary from 1 to 3.

For example, a neoplasm may be treated by applying a sufficient number of acoustic shock waves to the neoplasm. First the neoplasm is located in the patient. About 1000 to about 4000 acoustic shock waves are generated by applying a voltage potential across a spark gap of a spark gap generator ranging from about 14 kV to about 28 kV to generate each shock wave. These shock waves are applied to the neoplasm in a single treatment. In another embodiment, a sufficient number of acoustic shock waves are applied to treat a variety of ischemic conditions, such as bursitis. About 400 to about 3000 shock waves are applied per treatment. The shock waves are generated in the manner described above in this paragraph, and one or more treatments may be necessary for a positive response.

While the invention has been describe in terms of various preferred embodiments, those of skill in the art will appreciate that various modifications, substitutions, omissions and changes may be made without departing from the spirit thereof. Accordingly, it is intended that the scope of the present invention not be limited solely by the scope of the claims.

We claim:

1. A method of treating an ischemic condition associated with soft tissue adjacent to a musculo-skeletal environment, comprising:

locating a site or suspected site of the ischemic condition;

generating acoustic shock waves;

focusing the acoustic shock waves on the located site; and applying a sufficient number of acoustic shock waves to the located site to induce micro-injury and increased vascularization thereby inducing or accelerating healing.

2. The method of claim 1, wherein applying a sufficient number of acoustic shock waves comprises applying about 400 to about 3000 acoustic shock waves per treatment.

3. The method of claim 1, wherein the ischemic condition is bursitis.

4. The method of claim 1, wherein generating acoustic shock waves comprises applying a voltage potential across a spark gap of a spark gap generator ranging from about 14 kV to about 28 kV to generate each shock wave.

5. The method of claim 1, wherein applying a sufficient number of acoustic shock waves comprises applying the acoustic shock waves in a single treatment.

6. The method of claim 1, wherein the acoustic shock waves are focused on the located site with an ellipsoid reflector.

* * * * *

UNITED STATES PATENT AND TRADEMARK OFFICE
CERTIFICATE OF CORRECTION

PATENT NO.    : 6,390,995 B1
DATED         : May 21, 2002
INVENTOR(S)   : John A. Ogden et al.

It is certified that error appears in the above-identified patent and that said Letters Patent is hereby corrected as shown below:

<u>Title page,</u>
Item [54], Title, delete "MEDICAL CONDITIONS" and substitute -- AN ISCHEMIC CONDITION --

<u>Column 6,</u>
Line 24, delete "describe" and substitute -- described --

Signed and Sealed this

First Day of October, 2002

Attest:

Attesting Officer

JAMES E. ROGAN
Director of the United States Patent and Trademark Office